US010285611B1

(12) United States Patent
Harlev et al.

(10) Patent No.: US 10,285,611 B1
(45) Date of Patent: May 14, 2019

(54) CARDIAC MAPPING USING A 3D GRID

(71) Applicant: Boston Scientific Scimed Inc., Maple Grove, MN (US)

(72) Inventors: Doron Harlev, Brookline, MA (US); Daniel Klebanov, Arlington, MA (US); Alpar Csendes, Burlington, MA (US); Brian Stewart, North Reading, MA (US); Nathan H. Bennett, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 131 days.

(21) Appl. No.: 15/230,233

(22) Filed: Aug. 5, 2016

Related U.S. Application Data

(60) Provisional application No. 62/202,711, filed on Aug. 7, 2015.

(51) Int. Cl.
| | | |
|---|---|---|
| A61B 5/00 | (2006.01) |
| A61B 5/04 | (2006.01) |
| A61B 5/044 | (2006.01) |
| A61B 5/042 | (2006.01) |
| A61B 5/0452 | (2006.01) |
| A61B 5/0432 | (2006.01) |

(52) U.S. Cl.
CPC .......... *A61B 5/044* (2013.01); *A61B 5/04012* (2013.01); *A61B 5/0422* (2013.01); *A61B 5/0432* (2013.01); *A61B 5/0452* (2013.01); *A61B 5/7221* (2013.01)

(58) Field of Classification Search
CPC ... A61B 5/044; A61B 5/04012; A61B 5/0422; A61B 5/0432; A61B 5/0452; A61B 5/7221
See application file for complete search history.

(56) References Cited

U.S. PATENT DOCUMENTS

| | | | |
|---|---|---|---|
| 6,070,094 A | 5/2000 | Swanson et al. |
| 6,233,491 B1 | 5/2001 | Kordis et al. |
| 6,735,465 B2 | 5/2004 | Panescu |
| 7,515,954 B2 | 4/2009 | Harlev et al. |
| 8,103,338 B2 | 1/2012 | Harlev et al. |
| 8,428,700 B2 | 4/2013 | Harlev et al. |
| 8,615,287 B2 | 12/2013 | Harlev et al. |
| 8,948,837 B2 | 2/2015 | Harlev et al. |
| 2010/0286550 A1 | 11/2010 | Harlev et al. |
| 2015/0065836 A1 | 3/2015 | Thakur et al. |

*Primary Examiner* — Paula J Stice

(57) ABSTRACT

A system for facilitating display of cardiac mapping information includes a catheter having one or more electrodes that measure electrical signals in the heart, and a processing unit. The processing unit receives the electrical signals from the catheter and receives an indication of a measurement location corresponding to each signal. The processing unit extracts a set of features from the signals, where each feature includes a value corresponding to a metric. A three-dimensional grid is constructed, wherein each node of the grid corresponds to a physical point in three-dimensional space. The system identifies a set of electrical signals in a neighborhood associated with a node; determines, based on the set of features extracted from the set of electrical signals, a node value; associates the node value with the node; and facilitates presentation of a map corresponding to a cardiac surface based on the node value.

19 Claims, 10 Drawing Sheets

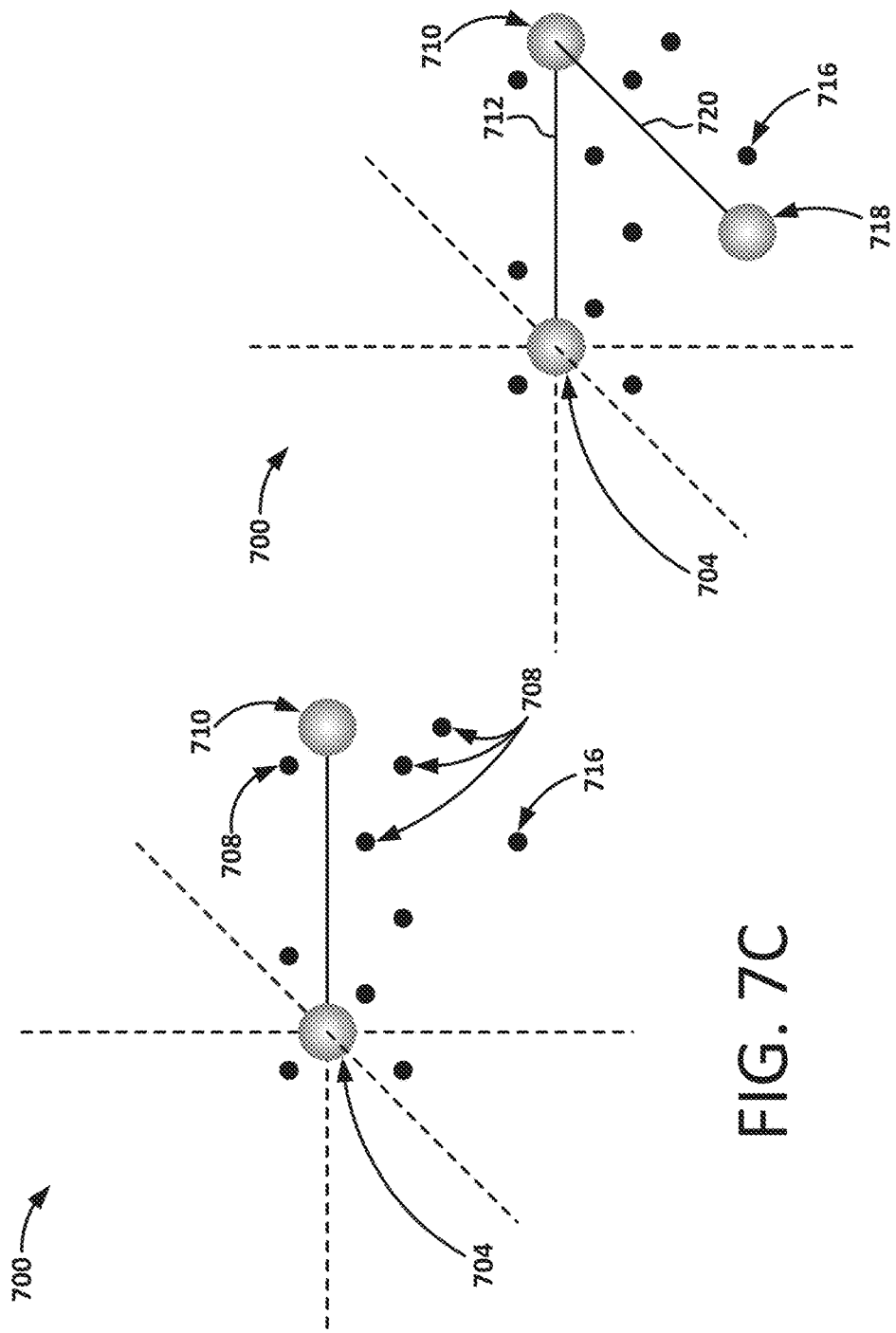

CARDIAC MAPPING USING A 3D GRID

CROSS-REFERENCE TO RELATED APPLICATION

This application claims priority to Provisional Application No. 62/202,711, filed Aug. 7, 2015, which is herein incorporated by reference in its entirety.

TECHNICAL FIELD

The present invention relates to medical systems and methods for mapping an anatomical space of the body. More specifically, the invention relates to systems and methods for cardiac mapping.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Conventional three-dimensional (3D) mapping techniques include contact mapping and non-contact mapping, and may employ a combination of contact and non-contact mapping. In both techniques, one or more catheters are advanced into the heart. With some catheters, once in the chamber, the catheter may be deployed to assume a 3D shape. In contact mapping, physiological signals resulting from the electrical activity of the heart are acquired with one or more electrodes located at the catheter distal tip after determining that the tip is in stable and steady contact with the endocardium surface of a particular heart chamber. In non-contact-based mapping systems, using the signals detected by the non-contact electrodes and information on chamber anatomy and relative electrode location, the system provides physiological information regarding the endocardium of the heart chamber. Location and electrical activity is usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm.

Though some modern systems now are capable of capturing thousands of data points during a mapping operation, many of the captured data points are not suitable for mapping, and to map thousands of data points may result in significant computational burdens. Thus, in some conventional systems, all of the points except those that are to be mapped are discarded, which results in waste and computation inefficiencies. For example, some conventional systems assume that the captured EGMs fall on the endocardium surface and test each EGM against adjacent EGMs to reject outliers, which may be computationally burdensome.

SUMMARY

Embodiments of the present invention use statistical techniques to determine the mapping values (voltage, time, etc.) that are used to build a map on a three-dimensional (3D) anatomy mesh. By aggregating events and applying statistical methods, embodiments of the invention may mitigate the influence of outliers and bad beats on a map, and allow the capture of a large number of data points, while improving computational efficiencies. According to embodiments, a Cartesian grid is formed in 3D space and mapping statistics are determined at the discrete nodes of the grid, based on nearby events measured in continuous space. These statistics are then used to deduce mapping values and project them onto the anatomy surface, which passes through the mesh. Because embodiments involve determining probability distributions associated with points in space, transformations (e.g., inverse transforms) need not necessarily be used to project points in space onto a mesh, which also may introduce computational efficiencies.

Although inferring statistics directly at mesh vertices may be desirable, embodiments of the grid-based system described herein may be implemented for computational efficiency. The anatomy mesh is constantly updated as a map is made, meaning that maintaining vertex-based statistics could be extremely computationally intensive, requiring a full re-run of the mapping process every time a new beat is added. By using a fixed grid, statistics can be maintained at each node and propagated to the mesh only when it comes close to any given node.

In an Example 1, a system for facilitating display of cardiac mapping information comprises: a mapping catheter comprising one or more electrodes that measure electrical signals in the heart; and a processing unit configured to: receive the plurality of electrical signals from the mapping catheter; receive an indication of a measurement location corresponding to each of the plurality of electrical signals; extract at least one feature from each of the plurality of electrical signals, wherein the at least one feature comprises at least one value corresponding to at least one metric; construct a three-dimensional grid having a plurality of nodes, wherein each of the plurality of nodes corresponds to a physical point in three-dimensional space; identify a set of electrical signals in a neighborhood associated with a node, wherein each of the set of electrical signals in the neighborhood has a corresponding measurement location that is located within a predetermined distance of the node; determine, based on the set of features extracted from the set of electrical signals, a node value; associate the node value with the node; and facilitate presentation of a map corresponding to a cardiac surface based on the node value.

In an Example 2, the system of Example 1, the measured electrical signals comprising a plurality of intracardiac electrograms (EGMs).

In an Example 3, the system of any of the preceding Examples, the at least one feature comprising at least one event, wherein the at least one event comprises the at least one value corresponding to the at least one metric and at least one corresponding time.

In an Example 4, the system of Example 3, the at least one metric comprising at least one of an activation time, an instantaneous potential, a voltage amplitude, a dominant frequency, and a peak-to-peak voltage.

In an Example 5, the system of any of Examples 3-4, wherein the processing unit is configured to determine the node value by: aggregating a set of features extracted from the set of electrical signals; computing a statistic associated with the aggregated set of features; and selecting the node value based on the computed statistic.

In an Example 6, the system of Example 5, wherein the statistic comprises at least one of a mode, a median, and a mean.

In an Example 7, the system of any of Examples 5 and 6, wherein the processing unit is configured to aggregate the set of features by including each of the features in a histogram.

In an Example 8, the system of any of Examples 5-7, wherein the processing unit is further configured to aggregate the set of features by: assigning a confidence level to the at least one event; determining a weighted confidence level; and including the weighted confidence level in a histogram.

In an Example 9, the system of Example 8, wherein the processing unit is configured to facilitate presentation of the map corresponding to the cardiac surface by performing an interpolation based on the histogram and at least one additional histogram corresponding to at least one additional node.

In an Example 10, the system of any of the preceding Examples, further comprising a display device configured to display the map corresponding to the cardiac surface.

In an Example 11, the system of any of the preceding Examples, wherein the map comprises at least one of a voltage map and an activation map.

In an Example 12, a method for facilitating display of cardiac mapping information comprises: receiving a plurality of electrical signals from a mapping catheter; receiving an indication of a measurement location corresponding to each of the plurality of electrical signals; extracting at least one feature from each of the plurality of electrical signals, wherein the at least one feature comprises at least one value corresponding to at least one metric; constructing a three-dimensional grid having a plurality of nodes, wherein each of the plurality of nodes corresponds to a physical point in three-dimensional space; identifying a set of electrical signals in a neighborhood associated with a node, wherein each of the set of electrical signals in the neighborhood has a corresponding measurement location that is located within a predetermined distance of the node; determining, based on the set of features extracted from the set of electrical signals, a node value; associating the node value with the node; and facilitating presentation of a map corresponding to a cardiac surface based on the node value.

In an Example 13, the method of Example 12, the measured electrical signals comprising a plurality of EGMs.

In an Example 14, the method of any of Examples 11-12, the at least one feature comprising at least one event, wherein the at least one event comprises the at least one value corresponding to the at least one metric and at least one corresponding time.

In an Example 15, the method of Example 14, wherein the at least one event comprises the at least one value corresponding to the at least one metric and at least one corresponding time, the step of determining the node value comprising: assigning a confidence level to the at least one event; determining a weighted confidence level; and including the weighted confidence level in a histogram.

In an Example 16, a system for facilitating display of cardiac mapping information comprises: a mapping catheter comprising one or more electrodes that measure electrical signals in the heart, the measured electrical signals comprising a plurality of EGMs; and a processing unit configured to: receive the plurality of EGMs from the mapping catheter; receive an indication of a measurement location corresponding to each of the EGMs; accept, based on one or more acceptance criteria, the plurality of EGMs; extract at least one feature from each of the plurality of EGMs, wherein the at least one feature comprises at least one value corresponding to at least one metric; construct a three-dimensional grid having a plurality of nodes, wherein each of the plurality of nodes corresponds to a physical point in three-dimensional space; identify a set of EGMs in a neighborhood associated with a node, wherein each of the set of EGMs in the neighborhood has a corresponding measurement location that is located within a predetermined distance of the node; aggregate a set of features extracted from the set of EGMs; compute a statistic associated with the aggregated set of features; associate the computed statistic with the node; and facilitate presentation of a map of a cardiac surface based on the statistic associated with the node.

In an Example 17, the system of Example 16, wherein the processing unit is configured to extract the at least one feature by identifying at least one event, wherein the at least one event comprises the at least one value corresponding to the at least one metric and at least one corresponding time.

In an Example 18, the system of Example 17, the at least one metric comprising at least one of an activation time, an instantaneous potential, a voltage amplitude, a dominant frequency, and a peak-to-peak voltage.

In an Example 19, the system of Example 17, wherein the processing unit is configured to determine the node value by: aggregating a set of features extracted from the set of electrical signals; computing a statistic associated with the aggregated set of features; and selecting the node value based on the computed statistic.

In an Example 20, the system of Example 19, wherein the processing unit is further configured to aggregate the set of features by: assigning a confidence level to the at least one event; determining a weighted confidence level; and including the weighted confidence level in a histogram.

In an Example 21, the system of Example 20, wherein the processing unit is further configured to convolve the histogram with a spreading function.

In an Example 22, the system of Example 16, wherein the processing unit is configured to facilitate presentation of the map corresponding to the cardiac surface by performing an interpolation based on the histogram and at least one additional histogram corresponding to at least one additional node to determine a mapping value corresponding to a vertex of an anatomy mesh.

In an Example 23, the system of Example 22, wherein the physical three-dimension location of the vertex is located within a cube defined by eight nodes and edges drawn between pairs of the eight nodes, wherein the processing unit is further configured to determine the mapping value by performing the interpolation based on the node value of each of the eight nodes.

In an Example 24, the system of Example 16, further comprising a display device configured to display the map corresponding to the cardiac surface.

In an Example 25, the system of any of the preceding Examples, wherein the map comprises at least one of a voltage map and an activation map.

In an Example 26, a method for facilitating display of cardiac mapping information comprises: receiving a plurality of electrical signals from a mapping catheter; receiving an indication of a measurement location corresponding to each of the plurality of electrical signals; extracting at least one feature from each of the plurality of electrical signals, wherein the at least one feature comprises at least one value corresponding to at least one metric; constructing a three-dimensional grid having a plurality of nodes, wherein each of the plurality of nodes corresponds to a physical point in three-dimensional space; identifying a set of electrical signals in a neighborhood associated with a node, wherein each of the set of electrical signals in the neighborhood has a corresponding measurement location that is located within a predetermined distance of the node; aggregating the set of features extracted from the set of electrical signals; determining, based on the aggregated set of features extracted from the set of electrical signals, a node value; associating the node value with the node; and facilitating presentation of a map corresponding to a cardiac surface based on the node value.

In an Example 27, the method of Example 26, wherein aggregating the set of features comprises: assigning a confidence level to each feature of the set of features; determining, for each feature of the set of features and based on a distance between the node and the measurement location corresponding to the electrical signal from which the feature was extracted, a weighted confidence level; and including each feature of the set of features in a bin of a histogram, wherein the contribution to the bin of the histogram is selected based on the weighted confidence level.

In an Example 28, the method of Example 27, wherein facilitating presentation of the map corresponding to the cardiac surface comprises performing an interpolation based on the histogram and at least one additional histogram corresponding to at least one additional node to determine a mapping value.

In an Example 29, the method of Example 26, wherein the map comprises at least one of a voltage map and an activation map.

In an Example 30, one or more computer-readable media having computer-executable instructions embodied thereon for facilitating display of cardiac mapping information, the computer-executable instructions configured to cause a processor, upon being executed by the processor, to instantiate at least one component, the at least one component comprises: a feature extractor configured to extract at least one feature from each of the plurality of electrical signals, wherein the at least one feature comprises at least one value corresponding to at least one metric; a grid generator configured to construct a three-dimensional grid having a plurality of nodes, wherein each of the plurality of nodes corresponds to a physical point in three-dimensional space; an aggregator configured to: identify a set of electrical signals in a neighborhood associated with a node, wherein each of the set of electrical signals in the neighborhood has a corresponding measurement location that is located within a predetermined distance of the node; determine, based on the set of features extracted from the set of electrical signals, a node value; and associate the node value with the node; and an interpolator configured to facilitate presentation of a map corresponding to a cardiac surface by performing an interpolation based on the node value to determine a mapping value.

In an Example 31, the media of Example 30, wherein the aggregator is further configured to aggregate the set of features by: assigning a confidence level to the at least one event; determining a weighted confidence level; and including the weighted confidence level in a histogram.

In an Example 32, the media of Example 31, wherein the aggregator is further configured to: convolve the histogram with a spreading function to smooth the histogram; and determine the node value by selecting, as the node value, the mode of the smoothed histogram.

In an Example 33, the media of Example 31, wherein the mapping value corresponds to a vertex of an anatomy mesh, and wherein the interpolator is configured to determine the mapping value by performing an interpolation based on the histogram and at least one additional histogram corresponding to at least one additional node.

In an Example 34, the media of Example 33, wherein the physical three-dimension location of the vertex is located within a cube defined by eight nodes and edges drawn between pairs of the eight nodes, wherein the processing unit is further configured to determine the mapping value by performing the interpolation based on the node value of each of the eight nodes.

In an Example 35, the media of Example 30, wherein the map comprises at least one of a voltage map and an activation map.

BRIEF DESCRIPTION OF THE DRAWINGS

FIGS. 7A-7F are conceptual diagrams depicting an illustrative process for using a 3D grid to facilitate display of cardiac information, in accordance with embodiments of the invention.

Figure 1:
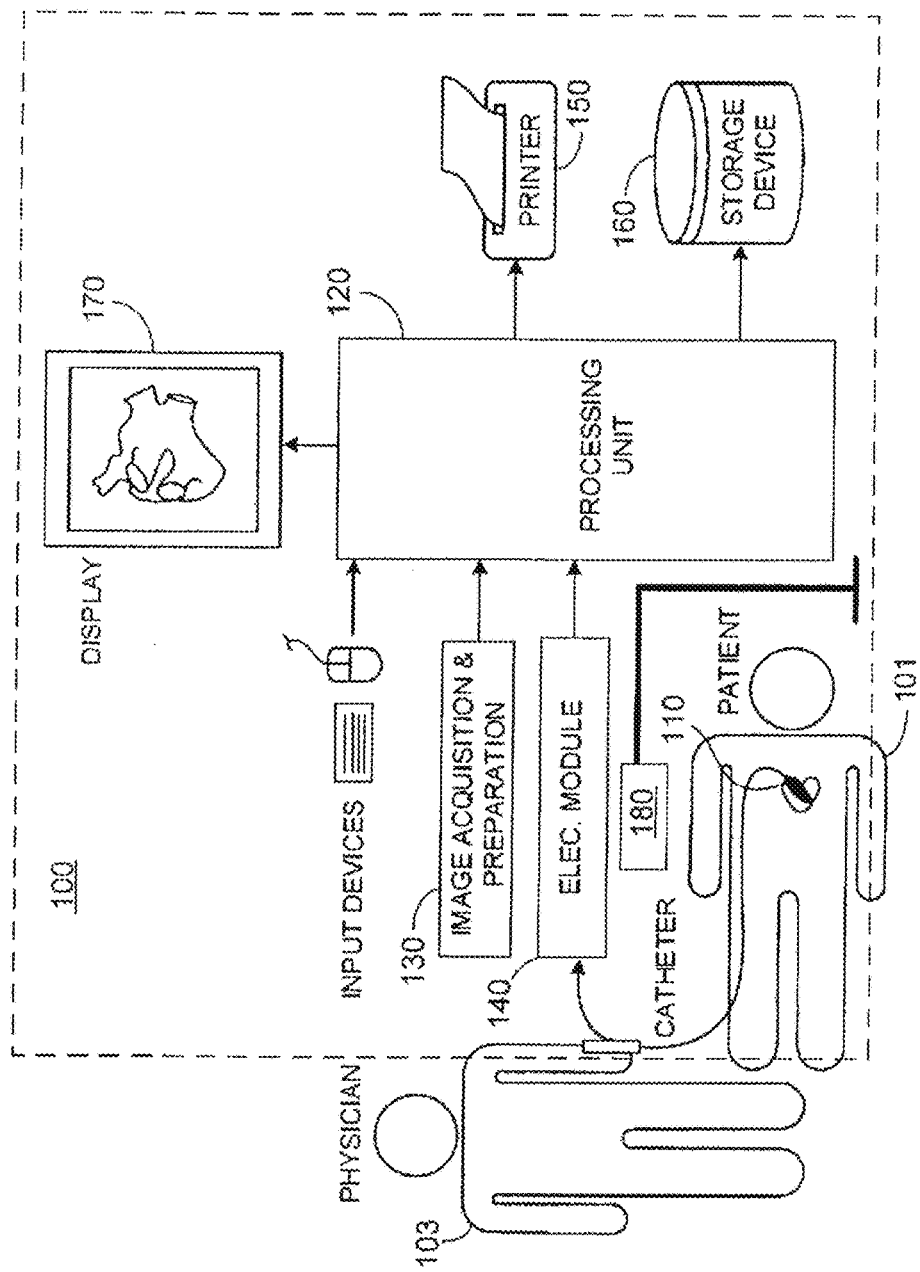
FIG. 1 is a conceptual diagram depicting an illustrative cardiac mapping system, in accordance with embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

FIG. 1 shows a schematic diagram of an exemplary embodiment of a cardiac mapping system 100. The mapping system 100 includes a moveable catheter 110 having multiple spatially distributed electrodes. During a signal-acquisition stage of a cardiac mapping procedure, the catheter 110 is displaced to multiple locations within the heart chamber into which the catheter 110 is inserted. In some embodiments the distal end of the catheter 110 is fitted with multiple electrodes spread somewhat uniformly over the catheter. For example, the electrodes may be mounted on the catheter 110 following a 3D olive shape, a basket shape, and/or the like. The electrodes are mounted on a device capable of deploying the electrodes into the desired shape while inside the heart, and retracting the electrodes when the catheter is removed from the heart. To allow deployment into a 3D shape in the heart, electrodes may be mounted on a balloon, shape memory material such as Nitinol, actuable hinged structure, and/or the like.

At each of the locations to which the catheter 110 is moved, the catheter's multiple electrodes acquire signals resulting from the electrical activity in the heart. Consequently, reconstructing and presenting to a user (such as a doctor and/or technician) physiological data pertaining to the heart's electrical activity may be based on information acquired at multiple locations, thereby providing a more accurate and faithful reconstruction of physiological behavior of the endocardium surface. The acquisition of signals at multiple catheter locations in the heart chamber enables the catheter to effectively act as a "mega-catheter" whose effective number of electrodes and electrode span is proportional to the product of the number of locations in which signal acquisition is performed and the number of electrodes the catheter has.

To enhance the quality of the reconstructed physiological information at the endocardium surface, in some embodiments the catheter 110 is moved to more than three locations (for example, more than 5, 10, or even 50 locations) within the heart chamber. Further, the spatial range over which the catheter is moved may be larger than one third (⅓) of the diameter of the heart cavity (for example, larger than 35%, 40%, 50% or even 60% of the diameter of the heart cavity). Additionally, in some embodiments the reconstructed physiological information is computed based on signals measured over several heart beats, either at a single catheter location within the heart chamber or over several locations. In circumstances where the reconstructed physiological information is based on multiple measurements over several heart beats, the measurements may be synchronized with one another so that the measurement are performed at approximately the same phase of the heart cycle. The signal measurements over multiple beats may be synchronized based on features detected from physiological data such as surface ECG and/or intracardiac electrograms (EGMs).

The cardiac mapping system 100 further includes a processing unit 120 which performs several of the operations pertaining to the mapping procedure, including the reconstruction procedure to determine the physiological information at the endocardium surface (e.g., as described above) and/or within a heart chamber. The processing unit 120 also may perform a catheter registration procedure. The processing unit 120 also may generate a 3D grid used to aggregate the information captured by the catheter 110 and to facilitate display of portions of that information.

The location of the catheter 110 inserted into the heart chamber can be determined using a conventional sensing and tracking system 180 that provides the 3D spatial coordinates of the catheter and/or its multiple electrodes with respect to the catheter's coordinate system as established by the sensing and tracking system. These 3D spatial locations may be used in building the 3D grid. Embodiments of the system 100 use a hybrid location technology that combines impedance location with magnetic location technology. This combination may enable the system 100 to accurately track catheters that are connected to the system 100. Magnetic location technology uses magnetic fields generated by a localization generator positioned under the patient table to track catheters with magnetic sensors. Impedance location technology may be used to track catheters that may not be equipped with a magnetic location sensor, and may utilize surface ECG patches.

In embodiments, to perform a mapping procedure and reconstruct physiological information on the endocardium surface, the processing unit 120 may align the coordinate system of the catheter 110 with the endocardium surface's coordinate system. The processing unit 110 (or some other processing component of the system 100) may determine a coordinate system transformation function that transforms the 3D spatial coordinates of the catheter's locations into coordinates expressed in terms of the endocardium surface's coordinate system, and/or vice-versa. In embodiments, such a transformation may not be necessary, as embodiments of the 3D grid described herein may be used to capture contact and non-contact EGMs, and select mapping values based on statistical distributions associated with nodes of the 3D grid. The processing unit 120 also may perform post-processing operations on the physiological information to extract and display useful features of the information to the operator of the system 100 and/or other persons (e.g., a physician).

According to embodiments, the signals acquired by the multiple electrodes of catheter 110 are passed to the processing unit 120 via an electrical module 140, which may include, for example, a signal conditioning component. The electrical module 140 receives the signals communicated from the catheter 110 and performs signal enhancement operations on the signals before they are forwarded to the processing unit 120. The electrical module 140 may include signal conditioning hardware, software, and/or firmware that may be used to amplify, filter and/or sample intracardiac potential measured by one or more electrodes. The intracardiac signals typically have a maximum amplitude of 60 mV, with a mean of a few millivolts. In some embodiments the signals are bandpass filtered in a frequency range (e.g., 0.5-500 Hz) and sampled with analog to digital converters (e.g., with 15-bit resolution at 1 kHz). To avoid interference with electrical equipment in the room, the signal may be filtered to remove the frequency corresponding to the power supply (e.g., 60 Hz). Other types of signal processing operations such as spectral equalization, automatic gain control, etc. may also take place. For example, in embodiments, the intracardiac signals may be unipolar signals, measured relative to a reference (which may be a virtual reference) such as, for example, a coronary sinus catheter or Wilson's Central Terminal (WCT), from which the signal processing operations may compute differences to generate bipolar signals. The signals may be otherwise processed (e.g., filtered, sampled, etc) before and/or after generating the bipolar signals. The resultant processed signals are forwarded by the module 140 to the processing unit 120 for further processing.

As further shown in FIG. 1, the cardiac mapping system 100 also may include peripheral devices such as a printer 150 and/or display device 170, both of which may be interconnected to the processing unit 120. Additionally, the mapping system 100 includes storage device 160 that may be used to store data acquired by the various interconnected modules, including the volumetric images, raw data measured by electrodes and/or the resultant endocardium representation computed therefrom, the partially computed transformations used to expedite the mapping procedures, the reconstructed physiological information corresponding to the endocardium surface, and/or the like.

The illustrative cardiac mapping system 100 shown in FIG. 1 is not intended to suggest any limitation as to the scope of use or functionality of embodiments of the present invention. Neither should the illustrative cardiac mapping system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present invention. For example, the electrical module 140 may be integrated with the processing unit 120.

Figure 2:
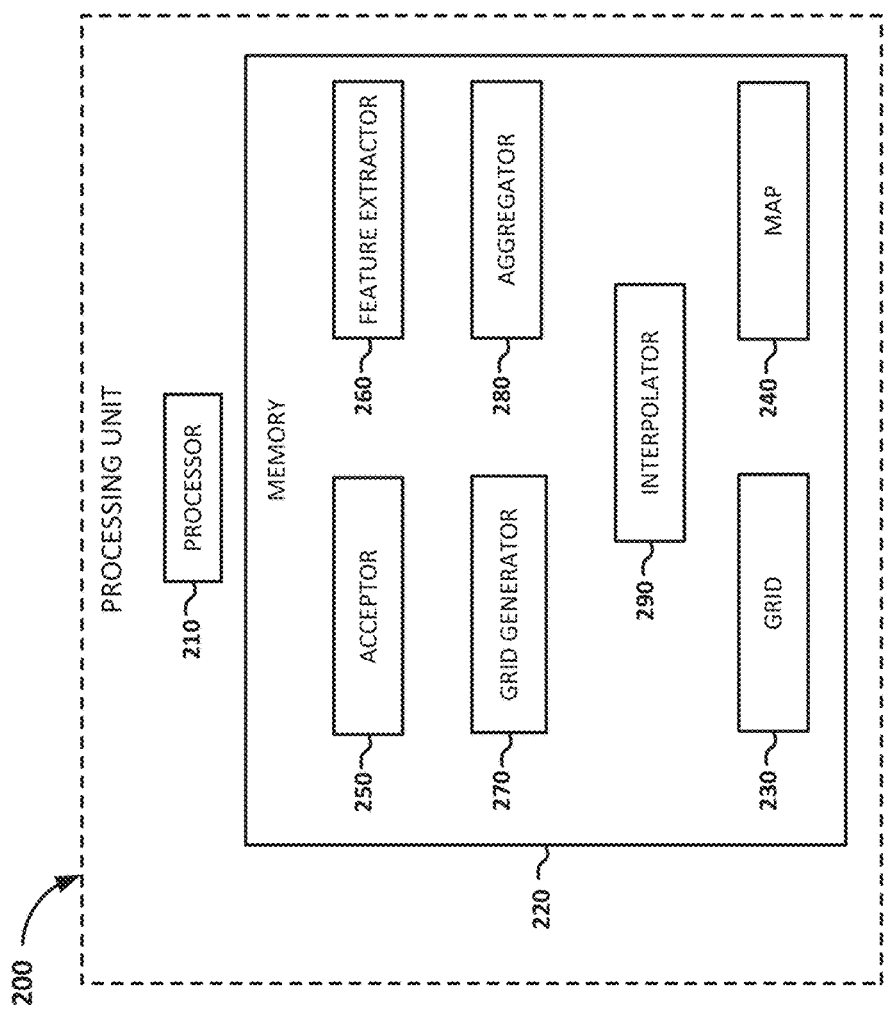
FIG. 2 is a block diagram depicting an illustrative processing unit for use with a cardiac mapping system, in accordance with embodiments of the present invention.

FIG. 2 is a block diagram of an illustrative processing unit 200, in accordance with embodiments of the invention. The processing unit 200 may be, be similar to, include, or be included in the processing unit 120 depicted in FIG. 1. As shown in FIG. 2, the processing unit 200 may be implemented on a computing device that includes a processor 210 and a memory 220. Although the processing unit 200 is referred to herein in the singular, the processing unit 200 may be implemented in multiple instances (e.g., as a server cluster), distributed across multiple computing devices, instantiated within multiple virtual machines, and/or the like. One or more components for facilitating cardiac mapping may be stored in the memory 220. In embodiments, the processor 210 may be configured to instantiate the one or more components to generate a grid 230, which may be used to construct a cardiac map 250, both of which may be stored in the memory 220.

As is further depicted in FIG. 2, the processing unit 200 may include an acceptor 250 configured to receive electrical signals from a mapping catheter (e.g., the mapping catheter 110 depicted in FIG. 1). The measured electrical signals may include a number of intracardiac electrograms (EGMs) sensed within a patient's heart. The acceptor 250 may also receive an indication of a measurement location corresponding to each of the electrical signals. In embodiments, the acceptor 250 may be configured to determine whether to accept the electrical signals that have been received. The acceptor 250 may utilize any number of different components and/or techniques to determine which electrical signals or beats to accept, such as filtering, beat matching, morphology analysis, positional information (e.g., catheter motion), respiration gating, and/or the like.

The accepted electrical signals are received by a feature extractor 260 that is configured to extract at least one feature from each of the electrical signals. In embodiments, the at least one feature includes at least one value corresponding to at least one metric. The at least one feature may include at least one event, where the at least one event includes the at least one value corresponding to the at least one metric and at least one corresponding time. According to embodiments, the at least one metric may include, for example, an activation time, minimum voltage value, maximum voltage value, maximum negative time-derivative of voltage, an instantaneous potential, a voltage amplitude, a dominant frequency, a peak-to-peak voltage, and/or the like.

As shown in FIG. 2, the processing unit 200 includes a grid generator 270 that is configured to construct a three-dimensional grid 230 having a number of nodes. The acceptor 250 and/or feature extractor 260 may generate, from the acquired electrical signals, a map dataset, which includes a number of events, stored in the grid 230. In embodiments, each node of the grid 230 corresponds to a physical point in 3D space. An aggregator 280 may be configured to identify a set of electrical signals in a neighborhood associated with a node, where each signal of the set of electrical signals in the neighborhood has a corresponding measurement location that is located within a predetermined distance of the node. In embodiments, a distance metric such as, for example, a rectilinear (Manhattan) distance may be calculated, and a weighting function (e.g., the weighting function described below with respect to FIG. 5) may be used to eliminate values outside of the desired Euclidean radius.

The aggregator 280 may be further configured to determine, based on the set of features extracted from the set of electrical signals, a node value. For example, the aggregator 280 may determine the node value by aggregating a set of features extracted from the set of electrical signals; computing a statistic associated with the aggregated set of features; and selecting the node value based on the computed statistic. In embodiments, the statistic may include a mode, a median, a mean, and/or the like.

The processing unit 200, using the aggregator 280, may be configured to aggregate the set of features by including each of the features in a histogram. For example, the aggregator 280 may be configured to aggregate the set of features by assigning a confidence level to each event corresponding to a feature; determining a weighted confidence level associated with each event; and including the weighted confidence levels in a histogram. The aggregator 280 may be further configured to associate the node value with the node.

As shown in FIG. 2, the processing unit 200 includes an interpolator 290 that is configured to facilitate presentation of a map 240 corresponding to a cardiac surface based on the node values. For example, the interpolator 290 may be configured to facilitate presentation of the map 240 corresponding to the cardiac surface by performing an interpolation based on a node value and at least one additional node value, and/or a histogram and at least one additional histogram corresponding to at least one additional node. In embodiments, the map 240 may include a voltage map, an activation map, a fractionation map, velocity map, confidence map, and/or the like.

The illustrative processing unit 200 shown in FIG. 2 is not intended to suggest any limitation as to the scope of use or functionality of embodiments of the present invention. Neither should the illustrative processing unit 200 be interpreted as having any dependency or requirement related to any single component or combination of components illustrated therein. Additionally, any one or more of the components depicted in FIG. 2 may be, in embodiments, integrated with various ones of the other components depicted therein (and/or components not illustrated), all of which are considered to be within the ambit of the present invention. For example, the acceptor 250 may be integrated with the feature extractor 260. Additionally, the processing unit 200 may (alone and/or in combination with other components of the system 100 depicted in FIG. 1, and/or other components not illustrated) perform any number of different functions and/or processes associated with cardiac mapping (e.g., triggering, blanking, field mapping, etc.) such as, for example, those described in U.S. Pat. No. 8,428,700, entitled "ELECTRO-ANATOMICAL MAPPING;" U.S. Pat. No. 8,948,837, entitled "ELECTROANATOMICAL MAPPING;" U.S. Pat. No. 8,615,287, entitled "CATHETER TRACKING AND ENDOCARDIUM REPRESENTATION GENERATION;" U.S. Pat. No. 9,737,227, entitled "ESTIMATING THE PREVALENCE OF ACTIVATION PATTERNS IN DATA SEGMENTS DURING ELECTROPHYSIOLOGY MAPPING;" U.S. Pat. No. 6,070,094, entitled "SYSTEMS AND METHODS FOR GUIDING MOVABLE ELECTRODE ELEMENTS WITHIN MULTIPLE-ELECTRODE STRUCTURE;" U.S. Pat. No. 6,233,491, entitled "CARDIAC MAPPING AND ABLATION SYSTEMS;" and U.S.

Pat. No. 6,735,465, entitled "SYSTEMS AND PROCESSES FOR REFINING A REGISTERED MAP OF A BODY CAVITY," the disclosures of which are hereby expressly incorporated herein by reference.

According to embodiments, various components of the mapping system 100, illustrated in FIG. 1, and/or the processing unit 200, illustrated in FIG. 2, may be implemented on one or more computing devices. A computing device may include any type of computing device suitable for implementing embodiments of the invention. Examples of computing devices include specialized computing devices or general-purpose computing devices such "workstations," "servers," "laptops," "desktops," "tablet computers," "handheld devices," "general-purpose graphics processing units (GPGPUs)," and the like, all of which are contemplated within the scope of FIGS. 1 and 2 with reference to various components of the system 100 and/or processing unit 200.

In embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in embodiments, the computing device may include a number of processors, a number of memory components, a number of I/O ports, a number of I/O components, and/or a number of power supplies. Additionally any number of these components, or combinations thereof, may be distributed and/or duplicated across a number of computing devices.

In embodiments, memory (e.g., the storage device 160 depicted in FIG. 1, and/or the memory 220 depicted in FIG. 2) includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 160 and/or 220 stores computer-executable instructions for causing a processor (e.g., the processing unit 120 depicted in FIG. 1 and/or the processor 210 depicted in FIG. 2) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Examples of such program components include the grid 230, the map 240, the acceptor 250, the feature extractor 260, the grid generator 270, the aggregator 280, and the interpolator 290. Program components may be programmed using any number of different programming environments, including various languages, development kits, frameworks, and/or the like. Some or all of the functionality contemplated herein may also, or alternatively, be implemented in hardware and/or firmware.

Figure 3:
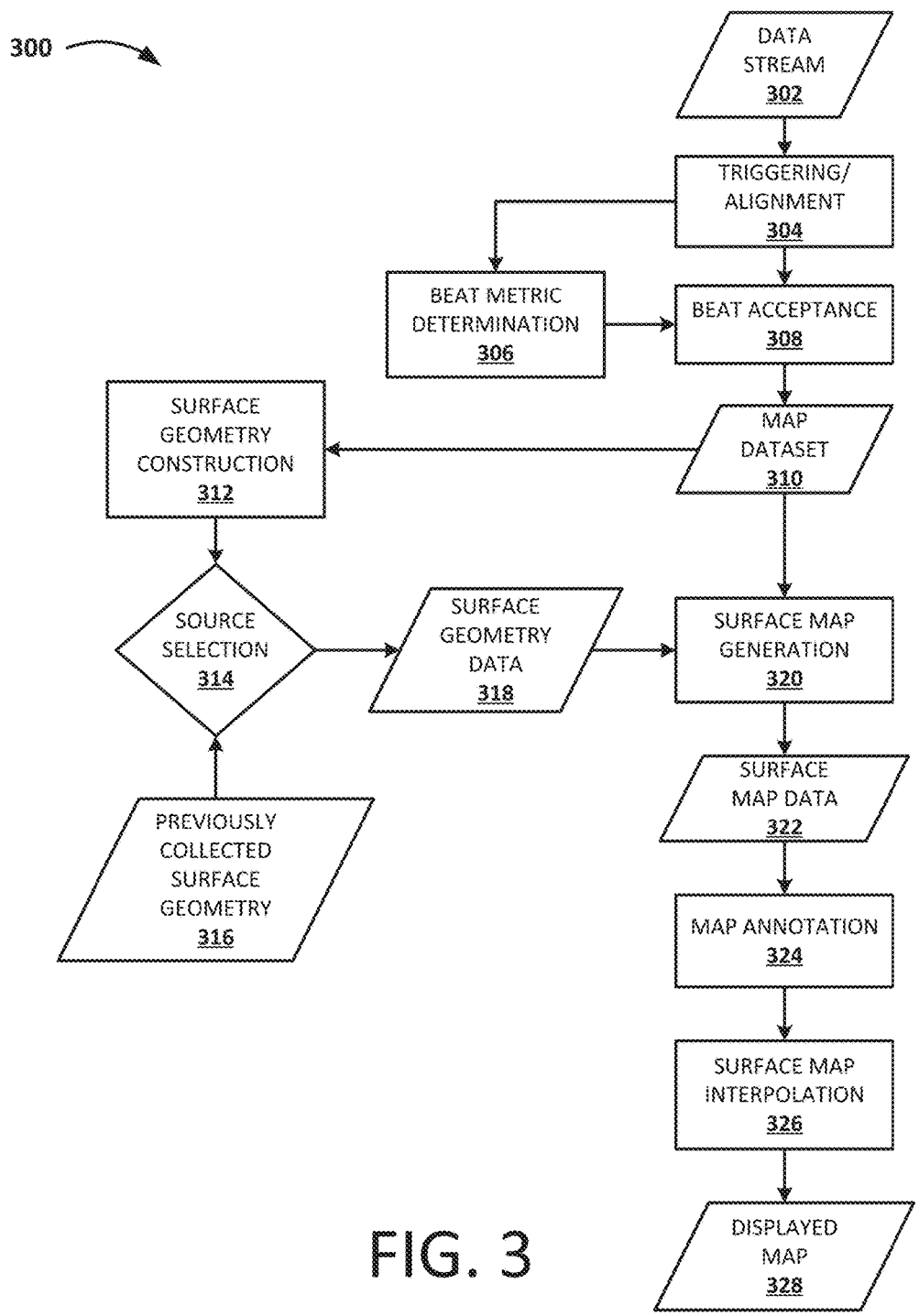
FIG. 3 is a flow diagram depicting an illustrative process for generating a cardiac map, in accordance with embodiments of the invention.

FIG. 3 is a flow diagram of an illustrative process 300 for automated electro-anatomical mapping, in accordance with embodiments of the invention. Aspects of embodiments of the method 300 may be performed, for example, by a processing unit (e.g., the processing unit 120 depicted in FIG. 1, and/or the processing unit 200 depicted in FIG. 2). A data stream 302 containing multiple signals is first input into the system (e.g., the cardiac mapping system 100 depicted in FIG. 1). During the automated electro-anatomical mapping process, a data stream 302 provides a collection of physiological and non-physiological signals that serve as inputs to the mapping process. The signals may be collected directly by the mapping system, and/or obtained from another system using an analog or digital interface. The data stream 302 may include signals such as unipolar and/or bipolar intracardiac electrograms (EGMs), surface electrocardiograms (ECGs), electrode location information originating from one or more of a variety of methodologies (magnetic, impedance, ultrasound, real time MRI, etc.), tissue proximity information, catheter force and/or contact information obtained from one or more of a variety of methodologies (force spring sensing, piezo-electric sensing, optical sensing etc.), catheter tip and/or tissue temperature, acoustic information, catheter electrical coupling information, catheter deployment shape information, electrode properties, respiration phase, blood pressure, other physiological information, and/or the like.

For the generation of specific types of maps, one or more signals may be used as one or more references, during a triggering/alignment process 304, to trigger and align the data stream 302 relative to the cardiac, other biological cycle and/or an asynchronous system clock resulting in beat datasets. Additionally, for each incoming beat dataset, a number of beat metrics are computed during a beat metric determination process 306. Beat metrics may be computed using information from a single signal, spanning multiple signals within the same beat and/or from signals spanning multiple beats. The beat metrics provide multiple types of information on the quality of the specific beat dataset and/or likelihood that the beat data is good for inclusion in the map dataset. A beat acceptance process 308 aggregates the criteria and determines which beat datasets will make up the map dataset 310. As explained herein, the map dataset 310 may be stored in association with a 3D grid that is dynamically generated during data acquisition.

Surface geometry data may be generated concurrently during the same data acquisition process using identical and/or different triggering and/or beat acceptance metrics employing a surface geometry construction process 312. This process constructs surface geometry using data such as electrode locations and catheter shape contained in the data stream. Additionally, or alternatively, previously collected surface geometry 316 may be used as an input to surface geometry data 318. Such geometry may have been collected previously in the same procedure using a different map dataset, and/or using a different modality such as CT, MRI, ultrasound, rotational angiography, and/or the like, and registered to the catheter locating system. The system performs a source selection process 314, in which it selects the source of the surface geometry data and provides surface geometry data 318 to a surface map generation process 320. The surface map generation process 320 is employed to generate surface map data 322 from the map dataset 320 and surface geometry data 318.

The surface geometry construction algorithm generates the anatomical surface on which the electroanatomical map is displayed. Surface geometry can be constructed, for example, using aspects of a system as described U.S. Pat. No. 8,103,338, entitled "Impedance Based Anatomy Generation" and filed on May 8, 2008; and/or U.S. Pat. No. 8,948,837, entitled "Electroanatomical Mapping" and issued on Feb. 3, 2015, the contents of each of which is incorporated by reference herein in its entirety. Additionally, or alternatively, an anatomical shell can be constructed by the processing unit by fitting a surface on electrode locations that are determined either by the user or automatically to be on the surface of the chamber. In addition, a surface can be fit on the outermost electrode and/or catheter locations within the chamber.

As described, the map dataset 320 from which the surface is constructed can employ identical or different beat acceptance criteria from those used for electrical and other types of maps. The map dataset 320 for surface geometry construction can be collected concurrently with electrical data or separately. Surface geometry can be represented as a mesh containing a collection of vertices (points) and the connectivity between them (e.g. triangles). Alternatively, surface geometry can be represented by different functions such as higher order meshes, non-uniform rational basis splines (NURBS), and/or curvilinear shapes.

The generation process 320 generates surface map data 322. The surface map data 322 may provide information on cardiac electrical excitation, cardiac motion, tissue proximity information, tissue impedance information, force information, and/or any other collected information desirable to the clinician. The combination of map dataset 320 and surface geometry data 318 allows for surface map generation. The surface map is a collection of values or waveforms (e.g., EGMs) on the surface of the chamber of interest, whereas the map dataset can contain data that is not on the cardiac surface. One approach for processing the map dataset 320 and surface geometry data 318 to obtain a surface map dataset 322 is described in U.S. Pat. No. 7,515,954, entitled "NON-CONTACT CARDIAC MAPPING, INCLUDING MOVING CATHETER AND MULTI-BEAT INTEGRATION" and filed Jun. 13, 2006, the contents of which is incorporated by reference herein in its entirety. Additionally, or alternatively, embodiments of the interpolation process may be used, as described herein, to generate the surface map based on aggregated events associated with nodes of the 3D grid.

Alternatively, or in combination with the method above, an algorithm that applies acceptance criteria to individual electrodes can be employed. For example, electrode locations exceeding a set distance (e.g., 3 mm) from surface geometry can be rejected. Another algorithm can incorporate tissue proximity information using impedance for inclusion in the surface map data. In this case only electrode location whose proximity value is less than 3 mm might be included. Additional metrics of the underlying data can also be used for this purpose. For example, EGM properties similar to beat metrics can be assessed on a per electrode basis. In this case metrics such as far field overlap and/or EGM consistency can be used. It should be understood that variations on the method to project points from the map dataset 320 to the surface and/or to select appropriate points can exist.

Once obtained, the surface map data 322 may be further processed to annotate desired features from the underlying data, a process defined as surface map annotation 324. Once data is collected into surface map data 322, attributes relating to the collected data may be automatically presented to the user. These attributes can be automatically determined and applied to the data by the computer system and are referred to herein as annotations. Exemplary annotations include activation time, the presence of double activation or fractionation, voltage amplitude, spectral content, and/or the like. Due to the abundance of data available in automated mapping (e.g., mapping completed by the computer system with minimal human input related to the incoming data), it is not practical for the operator to review and annotate data manually. However, human input can be a valuable addition to the data, and so when user input is provided it is necessary for the computer system to automatically propagate and apply it to more than one data point at a time.

It may be possible to use the computer system to automatically annotate activation time, voltage, and other characteristics of individual EGMs. Activation time detection may use methods similar to those previously described to detect a trigger and can similarly benefit from the use of blanking and powered triggering operator. Desired annotations may include instantaneous potential, activation time, voltage amplitude, dominant frequency and/or other properties of the signal. Once computed, the annotations may be displayed superimposed on chamber geometry. In embodiments, a gap-filling surface map interpolation may be employed 326. For example, in embodiments, a gap-filling interpolation may be employed where a distance between a point on the surface to a measured EGM exceeds a threshold, as this may indicate, for example, that grid-based interpolation, as described herein, may not be as effective in that situation. Displayed maps 328 can be computed and displayed separately, and/or overlaid on top of each other.

Figure 4:
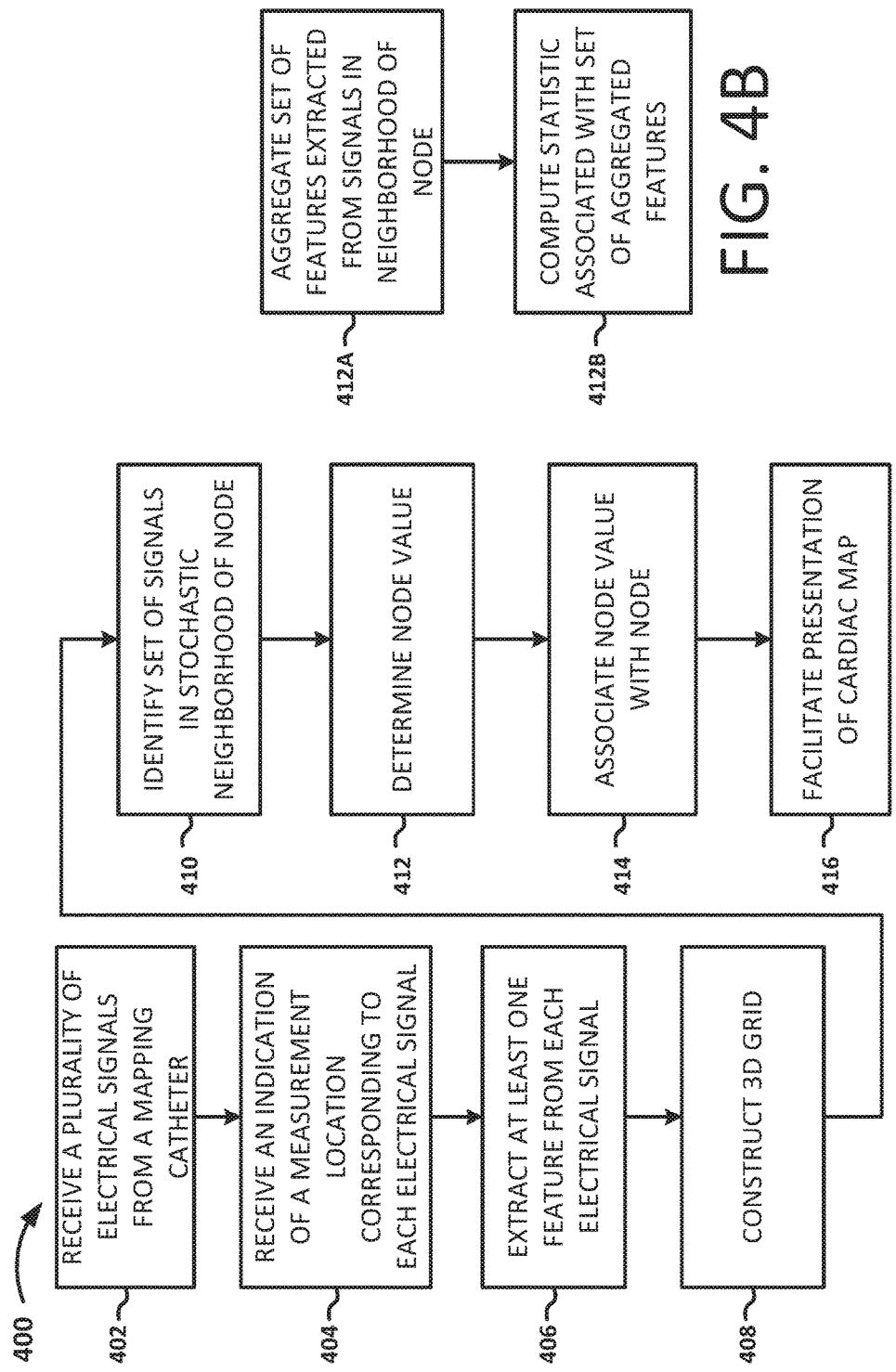
FIG. 4A is a flow diagram depicting an illustrative method of facilitating display of cardiac information, in accordance with embodiments of the invention.
FIG. 4B is a flow diagram depicting an illustrative method of determining a node value, in accordance with embodiments of the invention.

FIG. 4A is a flow diagram depicting an illustrative method 400 of facilitating display of cardiac mapping information, in accordance with embodiments of the invention. Aspects of embodiments of the method 400 may be performed, for example, by a processing unit (e.g., the processing unit 120 depicted in FIG. 1, and/or the processing unit 200 depicted in FIG. 2). Embodiments of the method 400 include receiving a plurality of electrical signals from a mapping catheter (block 402). The mapping catheter may be any catheter having one or more electrodes configured to obtain electrical signals (e.g., the mapping catheter 110 depicted in FIG. 1). The processing unit also receives an indication of a measurement location corresponding to each of the electrical signals (block 404). As explained above, with respect to FIG. 3, the processing unit and/or other components (e.g., the electrical module 140 depicted in FIG. 1) may be configured to determine whether to accept particular electrical signals (e.g., beats) based on one or more beat acceptance criteria.

Embodiments of the method 400 also include extracting at least one feature from each of the accepted electrical signals, where the at least one feature comprises at least one value corresponding to at least one metric (block 406). As described above, metrics may include any number of characteristics such as, for example, an activation time, an instantaneous potential, a voltage amplitude, a dominant frequency, a peak-to-peak voltage, and/or the like.

Embodiments of the method 400 further include constructing a three-dimensional (3D) grid having at least one node (block 408). Each node corresponds to a physical point in 3D space (block 408). In embodiments, the grid may be initialized such that it has a node placed at the origin of the coordinate system, which may, for example, correspond to a location at which measurements begin to be obtained. The grid may be expanded from the origin and, in embodiments, may have a fixed Grid Edge Length (GEL), which may be, for example, the length of grid cell edges (e.g., the length of an edge between two adjacent nodes), the corner-to-corner distance inside a cell (e.g., a length of an edge multiplied by the square root of three), and/or the like, and which may be equal along each axis, each direction, and/or the like. Setting the GEL too low may result in long computation times and/or undesirable burdens on the processing unit's memory. Setting the GEL too high may reduce the effective resolution of the map, as the stochastic radius increases with GEL (see below), thereby combining information from more widely-separated events.

For example, in embodiments, the GEL may be set to be between 1 mm and 3 mm, inclusive. In embodiments, the GEL may be set between 1.5 mm and 2 mm, and in some embodiments, the GEL may be, for example, 1.7 mm, 1.8 mm, or 2 mm. Any other desirable GEL may be used, and may be selected based on any number of various parameters associated with the mapping system. In embodiments, the value of GEL may be predetermined, calculated by the system, dynamic, user-adjustable, and/or the like. For example, in embodiments, the GEL may be set to a first value (e.g., 2 mm) for use in collecting most of the signals, but may be dynamically adjusted to a second, smaller, value (e.g., 1 mm) for areas of fine detail, or to a third, larger, value (e.g., 3 mm), for areas of less detail and/or fewer available measurements. In this manner, the GEL may be dynamically set, by the processing unit, during data acquisition, based on properties of the EGMs, the catheter, measurements, sampling, and/or the like. In embodiments, to enhance computational efficiencies, actual nodes may only be initialized as needed, in a sparse fashion, as information about the anatomy is obtained, thereby avoiding unnecessary computation and storage of statistics at unused nodes.

Figures 7A, 7B:
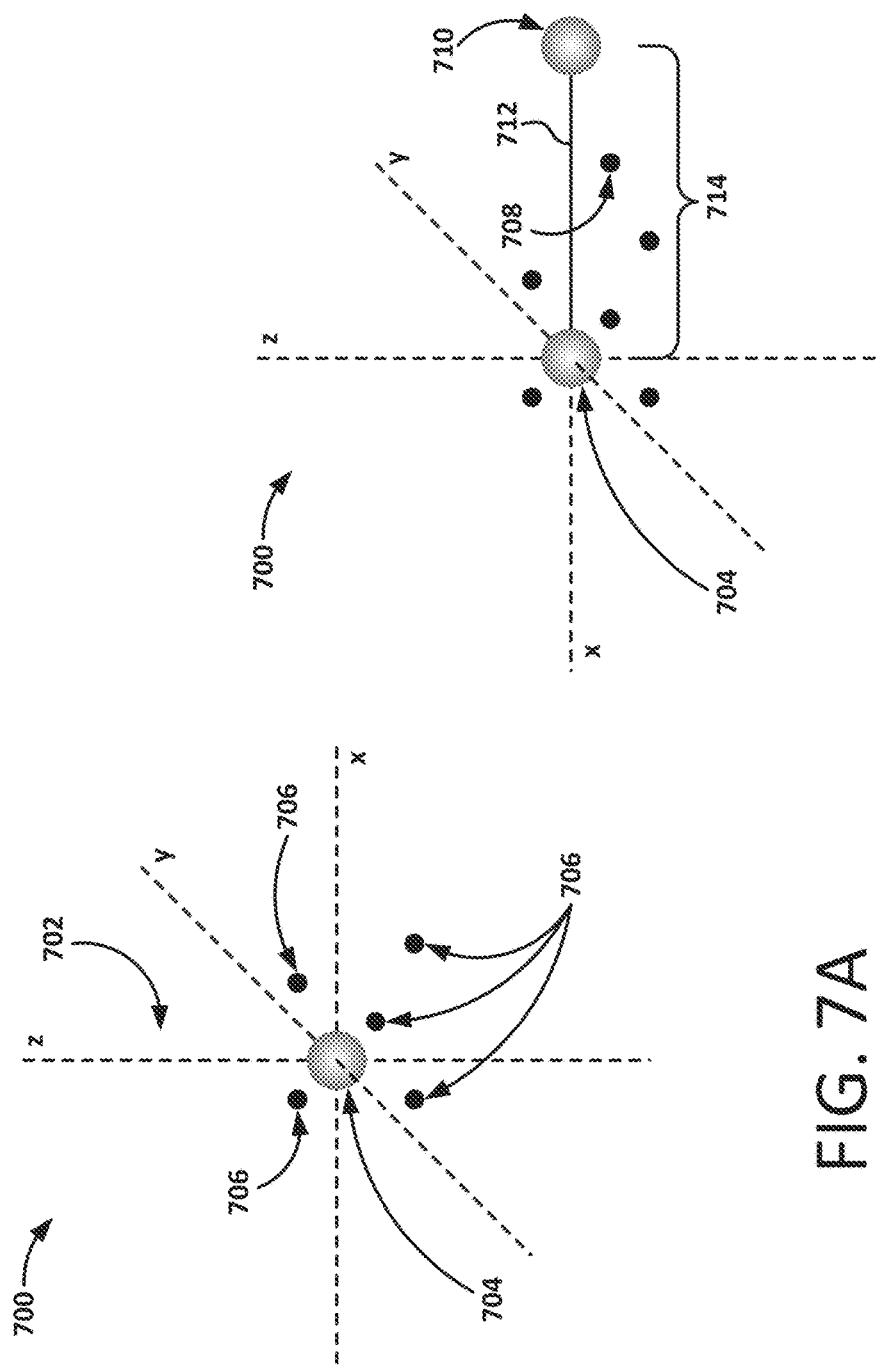

As an illustrative example, FIGS. 7A-7E are schematic depictions of generation of a three-dimensional grid 700 and use of that grid 700 to facilitate cardiac mapping. As shown in FIG. 7A, the grid 700 is initialized by establishing a first node 704 at the origin of a coordinate system 702. Although, in embodiments, other types of coordinate systems capable of representing three-dimensional space may be utilized, the illustrated coordinate system 702 is Cartesian and includes an x-axis, a y-axis, and a z-axis. As shown in FIG. 7A, events 706 may be within a predetermined distance (e.g., a stochastic radius (SR)) of the first node 704, and, when the node value corresponding to the first node 704 is calculated, each of the events 706 may influence that value.

In embodiments, the SR may be predetermined and/or fixed. In embodiments, the SR may be determined by calculating a maximum distance between two adjacent points on the grid, and/or may be configured to optimize the relevance of the aggregate values from the grid that are interpolated onto the anatomical mesh, thereby facilitating accurate mapping. The SR may be any type of distance between two points such as, for example, a rectilinear distance, L1, a Euclidean distance, L2, and/or the like. The SR may be adaptive and may be dynamically adjusted based on changes in a surface projection distance (SPD) (the maximum distance that an electrode can fall from the mesh surface and still be projected into the map, which may be set and/or adjusted to facilitate control over the accuracy of the map).

For example, in embodiments, only electrodes/events falling within the SPD are utilized in the mapping process. Additionally, in embodiments, to avoid the case where none of the grid nodes lying outside the anatomy have any events within their SR, it may be the case that: SR>GEL+SPD. In embodiments, for example, the relationship-determining SR may be predetermined in the engine so that SR=Y(GEL+SPD) where Y is a safety factor of greater than 1.

As explained above, additional nodes may be added to the grid 700 when needed for aggregating additional events. In embodiments, each event is associated with multiple nodes since SR>GEL+SPD. That is, for example, as shown in FIG. 7B, upon receiving an event 708 that is within the SR of a second node location, a second node 710 may be added such that the event 708 is within the SR of the second node 710. An edge 712 is also added between the first node 704 and the second node 710. In embodiments, the edge 712 may be only a conceptual construct, and not actually represented in the stored information. The position of the second node 710 may be established, for example, by requiring that it be one GEL 714 away from the first node 704, along one of the three axes. In embodiments, the second node 710 may be a distance away from the first node such that a corner-to-corner distance of a cubic cell including both nodes 704 and 710 is one GEL. Similarly, as shown in FIGS. 7C and 7D, additional events 708 may be within the stochastic radius of the second node 710, and only the first node 704 and second node 710 may be necessary until the system receives the event 716, which is also within the stochastic radius of a third node location. At that time, the system adds a third node 718, with a corresponding edge 720 extending between the second node 710 and the third node 718. In embodiments, the system may be configured to add grid nodes such that a node is created at every node location having a stochastic radius within which one or more events is located.

Figure 7E:
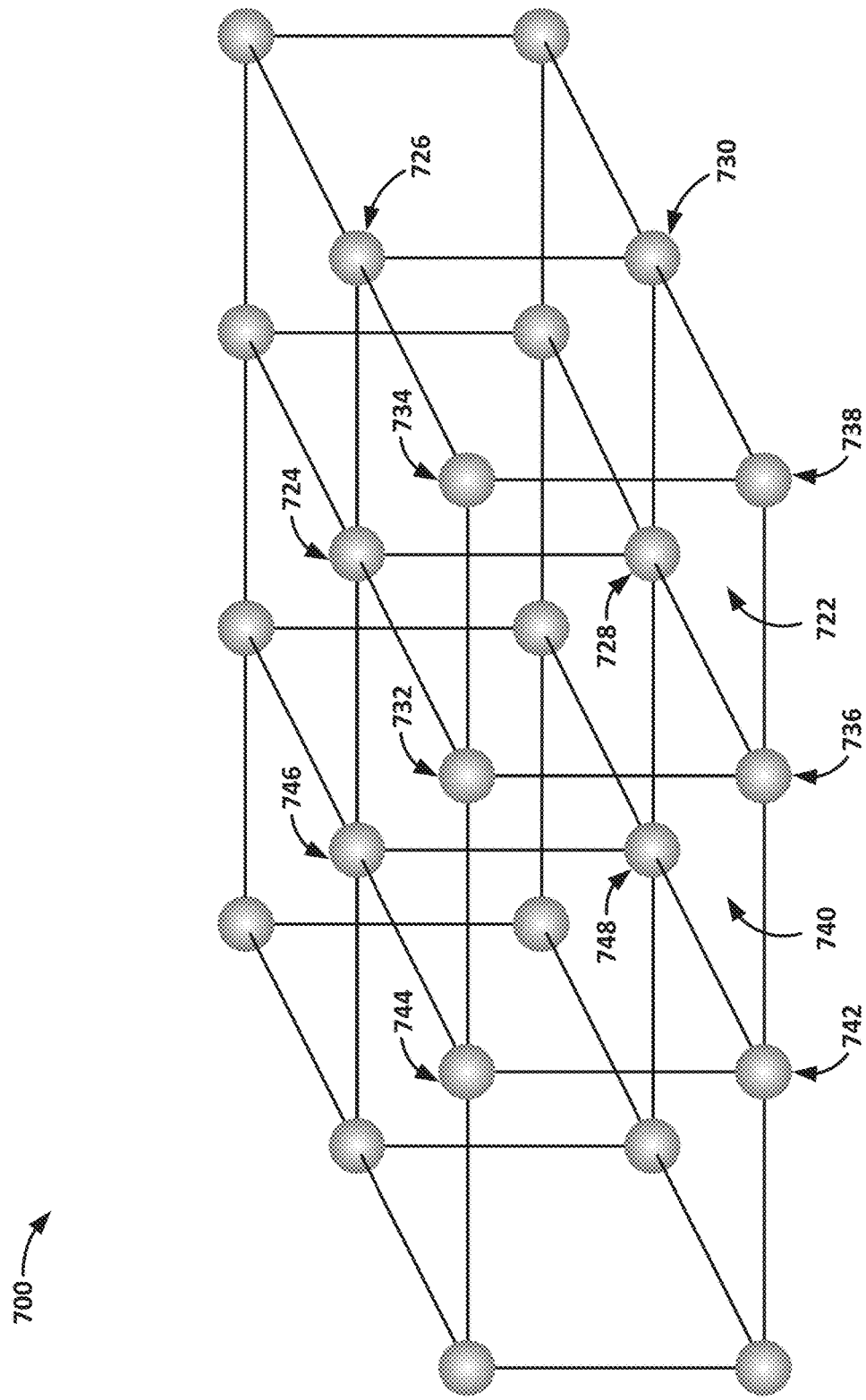

The process continues, according to embodiments of the invention, until a grid 700 is completed, as shown, for example, in FIG. 7E. As shown in FIG. 7E, as the grid 700 grows, cubic cells are defined by sets of eight nodes. For example, as shown, a first cell 722 is defined by the nodes 724, 726, 728, 730, 732, 734, 736, and 738, as well as the corresponding edges extending between adjacent ones of the nodes 724, 726, 728, 730, 732, 734, 736, and 738. Similarly, an adjacent cell 740 is defined by the nodes 724, 728, 732, 736, 742, 744, 746, and 748, as well as the corresponding edges extending between adjacent ones of the nodes 724, 728, 732, 736, 742, 744, 746, and 748. Note that the cells 722 and 740 share a set of four nodes, 724, 728, 732, and 736. In embodiments, the grid 700 may continue to be dynamic such that, at any time additional data is added to the map dataset (e.g., the map dataset 320 depicted in FIG. 3), additional nodes may be added to the grid 700.

Returning to FIG. 4A, embodiments of the method 400 further include identifying a set of electrical signals in a neighborhood associated with a node (block 410). According to embodiments, each of the set of electrical signals in the neighborhood has a corresponding measurement location that is located within a predetermined distance of the node. As explained above, the predetermined distance may be referred to as the stochastic radius (SR), and may be a fixed Euclidean distance from the node in all directions.

As shown in FIG. 4A, embodiments of the method 400 include determining, based on the set of features extracted from the set of electrical signals, a node value (block 412). As shown in FIG. 4B, the node value may be determined by aggregating a set of features extracted from the set of electrical signals in the neighborhood of the node (e.g., within the SR of the node) (block 412A) and computing a statistic associated with the set of aggregated features (block 412B). According to embodiments, the statistic may include, for example, a median, a mode, a mean, and/or the like. Aspects of an illustrative method for determining the node value, using a histogram, are presented in FIG. 5 and described in further detail below.

As shown in FIG. 4A, embodiments of the method 400 include associating the node value with the node (block 414), and facilitating presentation of a map corresponding to a cardiac surface based on the node value (block 416). The map may be a voltage map, an activation map, a fractionation map, velocity map, confidence map, and/or the like. According to embodiments, a node value may be used to determine mapping values where the anatomy mesh is within a certain distance of the node. For example, in embodiments, the information used to assign a mapping value to any given vertex on the anatomy mesh may be derived from the eight grid nodes that make up the cell within which the vertex falls.

Figure 7F:
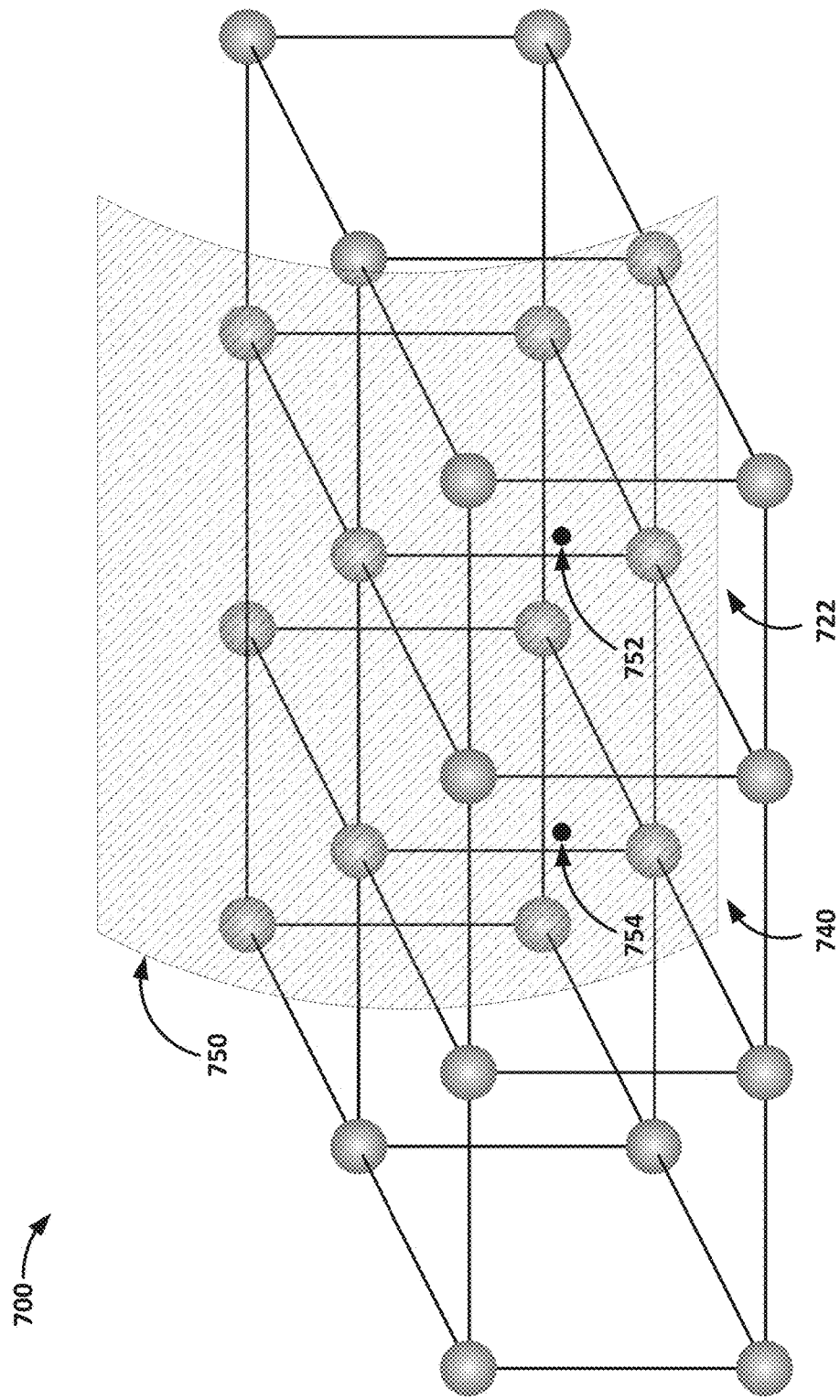

As shown, for example, in FIG. 7F, an anatomy mesh 750 may intersect the grid 700. A first vertex 752 of the mesh 750 is positioned within the first cell 722, and a second vertex 754 of the mesh 750 is positioned within the second cell 740. Because the physical three-dimension location of the first vertex 752 is located within a cube (cell) 722 defined by eight nodes 724, 726, 728, 730, 732, 734, 736, and 738 (as shown in FIG. 7E), and edges drawn between adjacent pairs of the eight nodes, the processing unit may be configured to determine the mapping value to be associated with the first vertex 752 by performing an interpolation based on the node value of each of the eight nodes 724, 726, 728, 730, 732, 734, 736, and 738. Similarly, because the physical three-dimension location of the second vertex 754 is located within a cube (cell) 740 defined by eight nodes 724, 728, 732, 736, 742, 744, 746, and 748 (as shown in FIG. 7E), and edges drawn between adjacent pairs of the eight nodes, the processing unit may be configured to determine the mapping value to be associated with the second vertex 754 by performing an interpolation based on the node value of each of the eight nodes 724, 728, 732, 736, 742, 744, 746, and 748. Note, that, because the cells 722 and 740 share a set of four nodes, 724, 728, 732, and 736, the node values associated with those four nodes will be part of the calculation of the mapping values for both the first vertex 752 and the second vertex 754.

According to embodiments, for example, to determine the mapping value to be associated with a vertex 752, the processing unit may first determine the node values of each of the eight nodes 724, 726, 728, 730, 732, 734, 736, and 738 of the cell 722 and determine the mapping value based on the node values themselves. In embodiments, the processing unit may determine the mapping value based on the histograms associated with each of the eight nodes 724, 726, 728, 730, 732, 734, 736, and 738. For example, node values may be determined at the eight individual nodes 724, 726, 728, 730, 732, 734, 736, and 738 and interpolated onto the mesh 750, or the histograms can be interpolated and a value picked from the interpolated histogram. According to embodiments, the interpolation, in either case, may include a tri-linear interpolation. In embodiments, a vertex that lies within a cell made up of one or more empty grid nodes (e.g., no event fell within the stochastic radius of the node) is not assigned a value directly. Instead, an interpolation may be run over the surface of the map so that the vertex value is assigned based on the values at the surrounding vertices.

In embodiments, a manual override may be utilized to select, or adjust, a mapping value. That is, for example, larger amplitude peaks may generally influence the mapping value selection more significantly than smaller amplitude peaks, but as a clinician reviews a displayed map, the clinician may prefer to have a smaller peak reflected on the map at a given mesh vertex. The clinician may, for example, recognize that, although the probability distribution led to selection of the larger peak, the smaller peak may be more accurate, or otherwise interesting, in a particular circumstance. Thus, the clinician may select the mapping value and replace it with the smaller peak. To account for this manual override, the system may be configured to replace one or more corresponding node values with the smaller peak, interpolate new values across the one or more nodes based on the smaller peak, and/or otherwise adjust affected node values (and/or adjacent node values) to reflect the manual override. In embodiments, the system may be configured to change the confidence value associated with the selected peak, in response to manual overriding. That is, for example, the system may assign a confidence value that is large enough such that it has the largest confidence of all non-manually overridden peaks within its neighborhood. In embodiments, density normalization may also be used in selecting a confidence value, as it may be desirable that the chosen confidence be invariant to regional measurement density. In embodiments, for example, the distribution associated with aggregated values about a particular node may be a bimodal distribution, in which case the user may be able to cause the system to switch between using a first mode as a node value to using the second mode as the node value.

Figure 5:
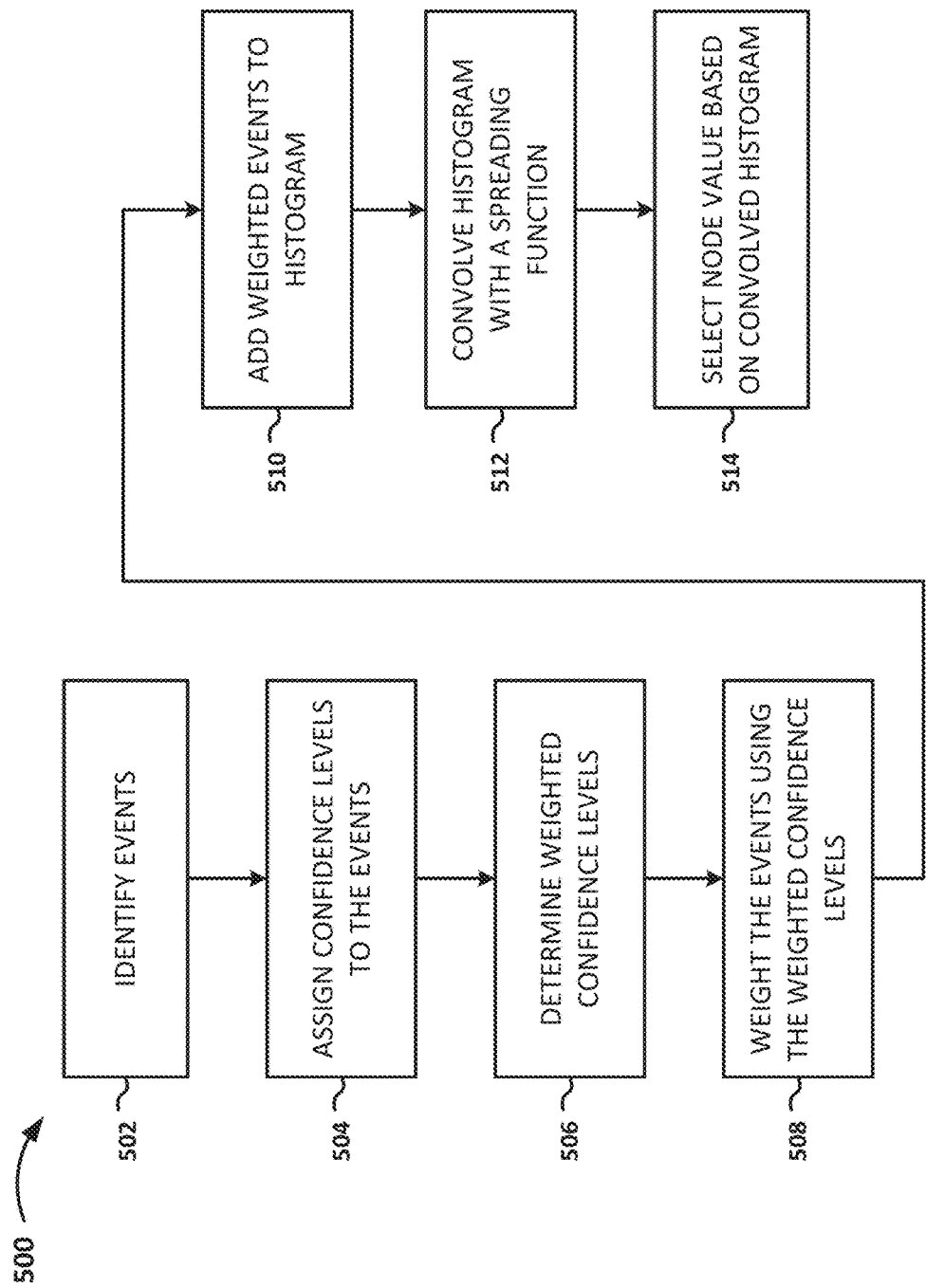
FIG. 5 is a flow diagram depicting another illustrative method of facilitating display of cardiac information, in accordance with embodiments of the invention.

FIG. 5 is a flow diagram depicting an illustrative method 500 of facilitating display of cardiac information, by determining a node value, in accordance with embodiments of the invention. Aspects of embodiments of the method 500 may be performed, for example, by a processing unit (e.g., the processing unit 120 depicted in FIG. 1, and/or the processing unit 200 depicted in FIG. 2). Embodiments of the method 500 described herein may be utilized in any number of different situations and to facilitate presenting any number of different types of maps. However, for clarity of explanation, further illustrative details are provided below with respect to the illustrative examples of creating activation maps and voltage maps. This discussion is not meant to limit the scope of the invention to only activation maps and voltage maps, and it is contemplated that aspects of the techniques described herein may be utilized in the context of fractionation maps, voltage maps, confidence maps, and/or the like.

As shown in FIG. 5, embodiments of the method 500 include identifying a number of events (block 502). In embodiments, an event includes at least one value corresponding to a metric and at least one corresponding time (e.g., the time at which the electrical signal from which the metric is derived was obtained). The metric may include an activation time, an instantaneous potential, a voltage amplitude, a dominant frequency, and a peak-to-peak voltage, and/or the like. In the examples discussed herein, for example, each event may include a time and a voltage activation value. In embodiments, events may be identified using a sorted peak detection process with a blanking window, which prevents a second event from being detected within a fixed duration of a higher amplitude event. More than one event may exist for any given electrode during any given beat. The number of events, $N_e$, per electrode per beat considered by the processing unit, $N_e$, is a parameter that may be predetermined, user-adjusted, dynamically adjusted, and/or the like. According to embodiments, events are detected in order of descending value of the metric (e.g., confidence, voltage, etc.) used to compute the event, until $N_e$ has been reached.

Embodiments of the method 500 further include assigning a confidence level to each event (block 504). For example, the confidence level, $C_i$, of an event i may be equal to the activation voltage in the case of activation mapping, and it may be equal to 1 in the case of voltage mapping. The confidence level, $C_i$, and the distance, $d_{ij}$, between the event i and a node j may determine how much influence the event has on the node.

The processing unit determines weighted confidence level for each node (block 506). In embodiments, confidence levels may be weighted using any number of different considerations such as, for example, electrode properties, measurement error, distance considerations, and/or the like. For example, a metric associated with a degree of confidence about whether the catheter was contacting the cardiac wall while a particular event was obtained may be used to weight the event confidence levels. Such a metric may be determined using, for example, an impedance-based system and/or other systems and/or techniques. In embodiments, the metric associated with whether the catheter was contacting the cardiac wall may also, or alternatively, be used as a filtering factor to determine whether to store the particular event.

In embodiments, for example, for a given node, the confidence level of each event falling within the stochastic radius may be weighted according to a distance weighting function, w=w(d). In embodiments, this function may be defined as:

$$w(d) = \begin{cases} 1 - \dfrac{d}{SR} & \text{for } 0 \leq d \leq SR; \\ 0 & \text{otherwise} \end{cases}$$

where d is the Euclidean distance between the node and the event in 3D space. So, in this example, for event i located within the stochastic radius of node j, the assigned weight would be:

$$w_{i,j} = 1 - \frac{\|P_i - P_j\|}{SR}$$

where $P_i$ and $P_j$ are the positions of the event and the node respectively. That is, for example, if the grid is constructed using Cartesian coordinates, the distance, $d_{ij}$, between the event i and the node j would be:

$$\sqrt{(x_i-x_j)^2+(y_i-y_j)^2+(z_i-z_j)^2}$$

where $P_i=(x_i, y_i, z_i)$ and $P_j=(x_j, y_j, z_j)$. The weighted confidence of event i with respect to node j may be:

$$C_{i,j}=w_{i,j}C_i$$

where $C_i$ is the un-weighted confidence level of event i. So that the sum of the weights associated with a particular node is equal to 1, a normalizing factor equal to the sum of the weights of all of the events within the stochastic radius may be used. However, for implementation purposes, this may not be applied until a mapping value is requested from the node, thereby enhancing computational efficiency. In this manner, further events that may come in at a later time may be added to the statistics without affecting the contribution of every previous event.

As is further shown in FIG. 5, embodiments of the method 500 include weighting the events using the weighted confidence levels (block 508) and adding the weighted events to a histogram (block 510). In embodiments, each weighted event within the stochastic radius of a particular node may be added to a histogram that is also associated with that node. In embodiments, the weights may be pre-normalized before adding the events to the histogram. In other embodiments, the weights are not pre-normalized. By not pre-normalizing the weights, it may be possible to simply accumulate bin values when new events fall within the stochastic radius of the node, thereby facilitating efficiently building a statistical representation of all the events influencing the node over time. According to embodiments, the histogram may, if graphed, include metric values along the x-axis (e.g., activation times, peak-to-peak EGM amplitude on a log scale, etc.) and the likelihood of the event on the y-axis. In embodiments, other techniques for aggregating information into a statistical distribution may be utilized instead of, or in addition to, a histogram.

In the case of activation mapping, a histogram associated with a node may include one bin for every time frame in the mapping window, where each bin contains the cumulative weighted confidence of all events occurring at the relevant frame. That is, for example, for the histogram, $h_j$, associated with node j:

$$h_j[k]=\Sigma_{\forall i:t_i=k} w_{i,j} C_{i0}$$

$$h_j[k] = \sum_{\forall i:t_i=k} w_{i,j} C_i$$

where k is the bin index and $t_i$ is the activation time frame associated with event i. For voltage mapping, the histogram may include a fixed number of bins that are equally spaced in a logarithmic space. For example, the histogram may include 100 bins with a range from 10 µV to 1.5V. Note that, to enhance computational efficiencies, 101 bins within the range may be generated and the last bin may be dropped to leave 100 bins. In embodiments, values outside the bin range may be added to the first or last bin as appropriate. Each bin may contain the cumulative weighted confidence of all events whose voltage falls within the bin range. Since, in the example of voltage mapping discussed above, the confidence of each event is set as 1, this devolves to the sum of the distance weights of each event within the bin:

$$h_j[k]=\Sigma w_{i,j} \; \forall i: b\text{Min}[k] \leq V_i < b\text{Max}[k]$$

where bMin[k] and bMax[k] denote the lower and upper limits of bin k respectively. Additionally, in some cases, a mapping catheter may be held in some places longer than others, moved more quickly in some regions than in others, and/or the like, resulting in varying levels of data density associated with different points on the grid. In embodiments, a metric related to density may be computed for each event before adding the event to the histogram so that the events added to the histogram may be adjusted (e.g., normalized) based on density, thereby minimizing undesirable skewing effects that density may have on the map.

As shown in FIG. 5, embodiments of the method 500 include convolving each histogram with a spreading function, g[k], which is used to allow the weighted events in the histogram to influence other events that are nearby in determining the node value (block 512). That is, the spreading function may be used such that dense clusters of points in nearby bins may be merged into a single strong group whilst outliers will have little impact on the result:

$$H_j[k] = (h_j * g)[k] = \sum_{m=-\infty}^{\infty} h[m]g[k-m]$$

The node value is selected based on the convolved histogram (block 514). For example, in embodiments, the node value that is selected is a value corresponding to the bin containing the resulting maximum:

$$\beta = \underset{k}{\operatorname{argmax}} H_j[k]$$

$$\alpha = c[\beta]$$

where β is a bin number, c is a vector of bin centers and α is the mapping value. In embodiments, the histogram may be smoothed and a center point may be selected. The center may actually refer to, for example, a median, a mode, a mean, and/or the like. In embodiments, the information may be aggregated into a continuous distribution and/or the histogram may be smoothed based on a continuous distribution, and any number of different statistical operators may be used to determine a value that has a high, or the highest, probability of occurring. That value may be selected as the node value. According to embodiments, instead of convolving the histogram using the spreading functions described above, other smoothing operations may be performed on the histogram. The convolving and/or smoothing operations may be adaptive.

Figure 6:
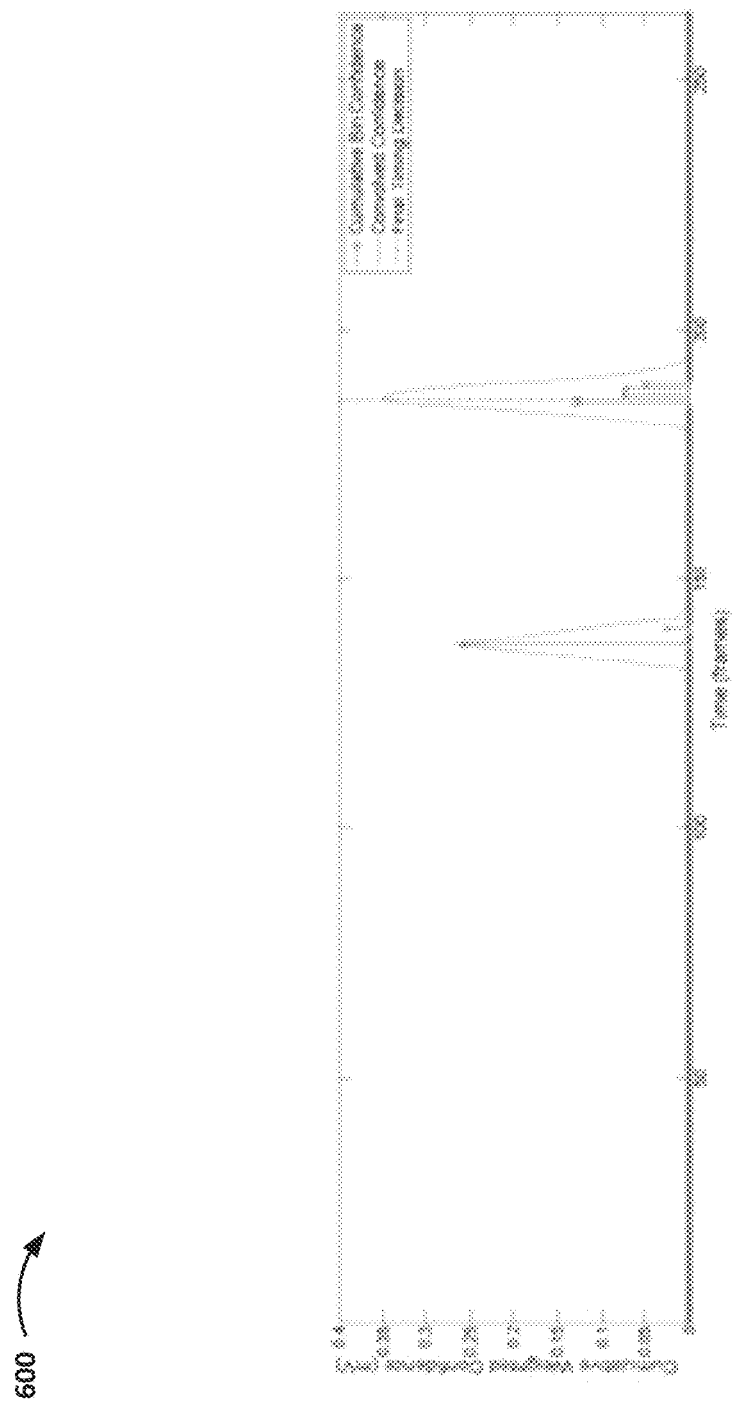
FIG. 6 is a graph showing an illustrative histogram associated with a grid node, in accordance with embodiments of the invention.

The spreading function may be any convolution function that is configured to allow the weighted events in the histogram to influence other events that are nearby in determining the node value. In the case of activation mapping, for example, the convolution function may be a symmetrical "triangle" function:

$$g[k] = \begin{cases} 1 - \frac{|k|}{\omega_c} & 0 \le k \le \omega_c \\ 0 & \text{otherwise} \end{cases}$$

where $\omega_c$ is the width of the convolution function in frames. Similarly, in the case of voltage mapping, the convolution function may be a symmetric function, as with activation mapping. FIG. 6 shows an example of a confidence histogram and convolution for a node in a human left atrial macro-reentrant tachycardia map (H3e, Map 1). In FIG. 6, following convolution, the mapping value gravitates towards a dense cluster of lower confidence events over a single, much higher confidence event (an outlier) occurring at a different time.

In embodiments, when mapping a macro-reentrant loop, the beginning and end of the mapping window may be taken to be essentially the same time. To handle these cases, circular convolution may be used when making activation maps, resulting in the low time bins influencing the high time bins and vice versa.

In embodiments, in the case of activation mapping, an event may include a measured value of an activation time (or, more accurately, an estimated activation time), and one or more error terms. That is, for example, the event may include three potential activation times to account for temporal uncertainty. Positional uncertainty may be accounted for by a dynamic SR. In embodiments, all three values may be used to increment a single bin of a node histogram, as if the system knew the actual activation time. The histogram could be convolved as each set of event data is added and/or during computation of node values and/or mapping values. Additionally, a user may manually override the selection of the activation time used for the node value and/or mapping value. For example, the user may select an EGM on the map, causing the system to display the selected activation time. The user may override the selected activation time, which may cause the system to update the 3D grid accordingly.

As indicated above, embodiments of aspects of the systems and methods described herein may be used for velocity mapping. A velocity map may provide information about the direction and speed of activation propagation. In embodiments, for example, the system may linearize a propagation along the catheter for a given EGM to determine an activation propagation vector (a "velocity vector"). A 3D grid, as described herein, may be used to aggregate the velocity vectors at a set of nodes. In that instance, for example, instead of the histogram at each node representing features along a single axis such as time, the histogram may represent the velocity vectors on a set of orthogonal axes, where a first axis (corresponding to an x-axis) represents an x-component of the velocity vector, a second axis (corresponding to a y-axis) represents a y-component of the velocity vector, and a third axis (corresponding to a z-axis) represents a z-component of the velocity vector. The vector-valued histogram may be smoothed across multiple dimensions before a node value is selected by determining, for example, the mode of the distribution. In other words, the methods described above for scalar-valued features can be applied similarly to vector-valued features. However, a sparse representation of the histogram may sometimes be more efficient. Instead of counting the occurrence of vector values in each vector bin, for example, the observed vector values may be stored, and smoothed results may be evaluated only at the observed vector values.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. For example, confidence associated with selected node values and/or mapping values may be determined and used to provide feedback, smoothing, and/or other optimizing processes. Accordingly, the scope of the present invention is intended to embrace all such alternatives, modifications, and variations as fall within the scope of the claims, together with all equivalents thereof.

We claim:

1. A system for facilitating display of cardiac mapping information, the system comprising:
    a mapping catheter comprising one or more electrodes that measure electrical signals in the heart, the measured electrical signals comprising a plurality of intracardiac electrograms (EGMs);
    a processing unit configured to:
        receive the plurality of EGMs from the mapping catheter;
        receive an indication of a measurement location corresponding to each of the EGMs;
        extract at least one feature from each of the plurality of EGMs, wherein the at least one feature comprises at least one value corresponding to at least one metric;
        construct a three-dimensional grid having a plurality of nodes, wherein each of the plurality of nodes corresponds to a physical point in three-dimensional space;
        identify a set of EGMs in a neighborhood associated with a node, wherein each of the set of EGMs in the neighborhood has a corresponding measurement location that is located within a predetermined distance of the node;
        determine a node value, wherein the processing unit is configured to determine the node value by:

aggregating a set of features extracted from the set of EGMs; and computing a statistic associated with the aggregated set of features;

associate the node value with the node; and facilitate presentation of a map of a cardiac surface and based on the node value associated with the node.

2. The system of claim 1, wherein the processing unit is configured to extract the at least one feature by identifying at least one event, wherein the at least one event comprises the at least one value corresponding to the at least one metric and at least one corresponding time.

3. The system of claim 2, the at least one metric comprising at least one of an activation time, an instantaneous potential, a voltage amplitude, a dominant frequency, and a peak-to-peak voltage.

4. The system of claim 1, wherein the processing unit is further configured to aggregate the set of features by:

assigning a confidence level to the at least one event;

determining a weighted confidence level; and including the weighted confidence level in a histogram.

5. The system of claim 4, wherein the processing unit is further configured to convolve the histogram with a spreading function.

6. The system of claim 1, wherein the processing unit is configured to facilitate presentation of the map corresponding to the cardiac surface by performing an interpolation based on the histogram and at least one additional histogram corresponding to at least one additional node to determine a mapping value corresponding to a vertex of an anatomy mesh.

7. The system of claim 6, wherein the physical three-dimension location of the vertex is located within a cube defined by eight nodes and edges drawn between pairs of the eight nodes, wherein the processing unit is further configured to determine the mapping value by performing the interpolation based on the node value of each of the eight nodes.

8. The system of claim 1, further comprising a display device configured to display the map corresponding to the cardiac surface, wherein the map comprises at least one of a voltage map, an activation map, and a fractionation map.

9. The system of claim 1, wherein the predetermined distance comprises a Euclidean distance or a rectilinear distance.

10. A method for facilitating display of cardiac mapping information, the method comprising:

receiving a plurality of electrical signals from a mapping catheter;

receiving an indication of a measurement location corresponding to each of the plurality of electrical signals;

extracting at least one feature from each of the plurality of electrical signals, wherein the at least one feature comprises at least one value corresponding to at least one metric;

constructing a three-dimensional grid having a plurality of nodes, wherein each of the plurality of nodes corresponds to a physical point in three-dimensional space;

identifying a set of electrical signals in a neighborhood associated with a node, wherein each of the set of electrical signals in the neighborhood has a corresponding measurement location that is located within a predetermined distance of the node;

determine a node value, wherein determining the node value comprises:

aggregating the set of features extracted from the set of electrical signals; and determining, based on the aggregated set of features extracted from the set of electrical signals, a node value;

associating the node value with the node; and facilitating presentation of a map corresponding to a cardiac surface and based on the node value.

11. The method of claim 10, wherein aggregating the set of features comprises:

assigning a confidence level to each feature of the set of features;

determining, for each feature of the set of features and based on a distance between the node and the measurement location corresponding to the electrical signal from which the feature was extracted, a weighted confidence level; and including each feature of the set of features in a bin of a histogram, wherein the contribution to the bin of the histogram is selected based on the weighted confidence level.

12. The method of claim 11, wherein facilitating presentation of the map corresponding to the cardiac surface comprises performing an interpolation based on the histogram and at least one additional histogram corresponding to at least one additional node to determine a mapping value.

13. The method of claim 10, wherein the map comprises at least one of a voltage map and an activation map.

14. One or more computer-readable media having computer-executable instructions embodied thereon for facilitating display of cardiac mapping information, the computer-executable instructions configured to cause a processor, upon being executed by the processor, to instantiate at least one component, the at least one component comprising:

a feature extractor configured to extract at least one feature from each of the plurality of electrical signals, wherein the at least one feature comprises at least one value corresponding to at least one metric a grid generator configured to construct a three-dimensional grid having a plurality of nodes, wherein each of the plurality of nodes corresponds to a physical point in three-dimensional space;

an aggregator configured to:

identify a set of electrical signals in a neighborhood associated with a node, wherein each of the set of electrical signals in the neighborhood has a corresponding measurement location that is located within a predetermined distance of the node;

determine, based on the set of features extracted from the set of electrical signals, a node value; and associate the node value with the node; and an interpolator configured to facilitate presentation of a map corresponding to a cardiac surface by performing an interpolation based on the node value to determine a mapping value.

15. The media of claim 14, wherein the aggregator is further configured to aggregate the set of features by:

assigning a confidence level to the at least one event;

determining a weighted confidence level; and including the weighted confidence level in a histogram.

16. The media of claim 15, wherein the aggregator is further configured to:

convolve the histogram with a spreading function to smooth the histogram; and determine the node value by selecting, as the node value, the mode of the smoothed histogram.

17. The media of claim 15, wherein the mapping value corresponds to a vertex of an anatomy mesh, and wherein the interpolator is configured to determine the mapping value by performing an interpolation based on the histogram and at least one additional histogram corresponding to at least one additional node.

18. The media of claim 17, wherein the physical three-dimension location of the vertex is located within a cube defined by eight nodes and edges drawn between pairs of the eight nodes, wherein the processing unit is further configured to determine the mapping value by performing the interpolation based on the node value of each of the eight nodes.

19. The media of claim 14, wherein the map comprises at least one of a voltage map and an activation map.

\* \* \* \* \*